US009352319B2

(12) United States Patent
Douglas et al.

(10) Patent No.: US 9,352,319 B2
(45) Date of Patent: May 31, 2016

(54) LIQUID DISPENSING DEVICE

(71) Applicant: TTP LabTech Limited, Melbourn, Royston, Hertfordshire (GB)

(72) Inventors: Anthony Douglas, Royston (GB); Gary Cochrane, Royston (GB)

(73) Assignee: TTP LabTech Limited, Melbourne, Royston, Hertfordshire (GB)

( * ) Notice: Subject to any disclaimer, the term of this patent is extended or adjusted under 35 U.S.C. 154(b) by 167 days.

(21) Appl. No.: 13/949,979

(22) Filed: Jul. 24, 2013

(65) Prior Publication Data

US 2014/0030166 A1    Jan. 30, 2014

(30) Foreign Application Priority Data

Jul. 26, 2012    (GB) .................................. 1213300.5

(51) Int. Cl.
| | | |
|---|---|---|
| B01L 3/00 | (2006.01) | |
| F02B 63/04 | (2006.01) | |
| B01L 3/02 | (2006.01) | |
| G01N 35/10 | (2006.01) | |

(52) U.S. Cl.
CPC ................ B01L 3/52 (2013.01); B01L 3/0227 (2013.01); B01L 3/0251 (2013.01); B01L 3/5085 (2013.01); F02B 63/044 (2013.01); B01L 2300/0829 (2013.01); F02B 2063/045 (2013.01); G01N 2035/1034 (2013.01); G01N 2035/1041 (2013.01)

(58) Field of Classification Search
CPC . B01L 3/52; B01L 3/0227; G01N 2035/1034; G01N 2035/1044; F02B 63/044

USPC ......... 422/501, 511, 509, 518, 521, 545–546; 73/863.32, 864, 864.01, 864.13, 73/864.16, 864.17
See application file for complete search history.

(56) References Cited

U.S. PATENT DOCUMENTS

| | | | | |
|---|---|---|---|---|
| 4,567,780 | A | * | 2/1986 | Oppenlander et al. ..... 73/864.16 |
| 4,830,832 | A | * | 5/1989 | Arpagaus et al. ............... 422/65 |
| 8,920,752 | B2 | * | 12/2014 | Tisone ................. B01J 19/0046 422/501 |
| 2007/0025880 | A1 | | 2/2007 | Hoummady |
| 2013/0291660 | A1 | * | 11/2013 | Wilmer ................... B01L 3/021 73/864.13 |
| 2014/0298925 | A1 | * | 10/2014 | Voyeux ................. B01L 3/0217 73/864.13 |

FOREIGN PATENT DOCUMENTS

| | | |
|---|---|---|
| EP | 1658894 | 5/2006 |
| EP | 2050499 | 4/2009 |
| JP | 2004245787 | 9/2004 |
| JP | 2006038661 | 2/2006 |
| WO | 2011083125 | 7/2011 |

OTHER PUBLICATIONS

Search Report dated Nov. 19, 2012, relating to British Application GB1213300.5.

* cited by examiner

*Primary Examiner* — Brian R Gordon
(74) *Attorney, Agent, or Firm* — Barnes & Thornburg LLP

(57) ABSTRACT

A droplet dispensing apparatus has a piston rod driven by a solenoid, the rod for connection to a piston of a droplet dispensing syringe, in which the output member from the solenoid is directly connected to the rod through the entire impulse produced by the solenoid.

17 Claims, 13 Drawing Sheets

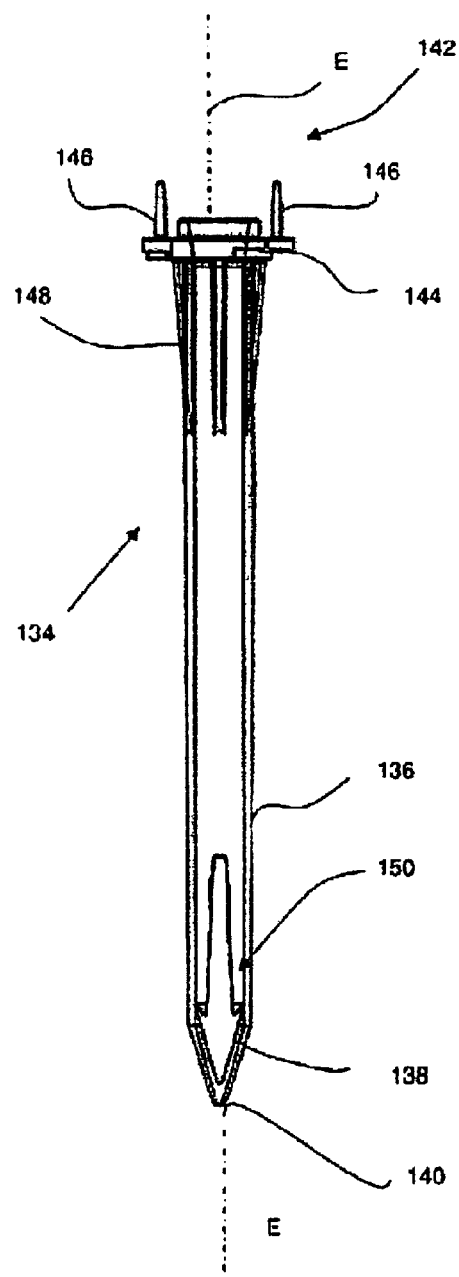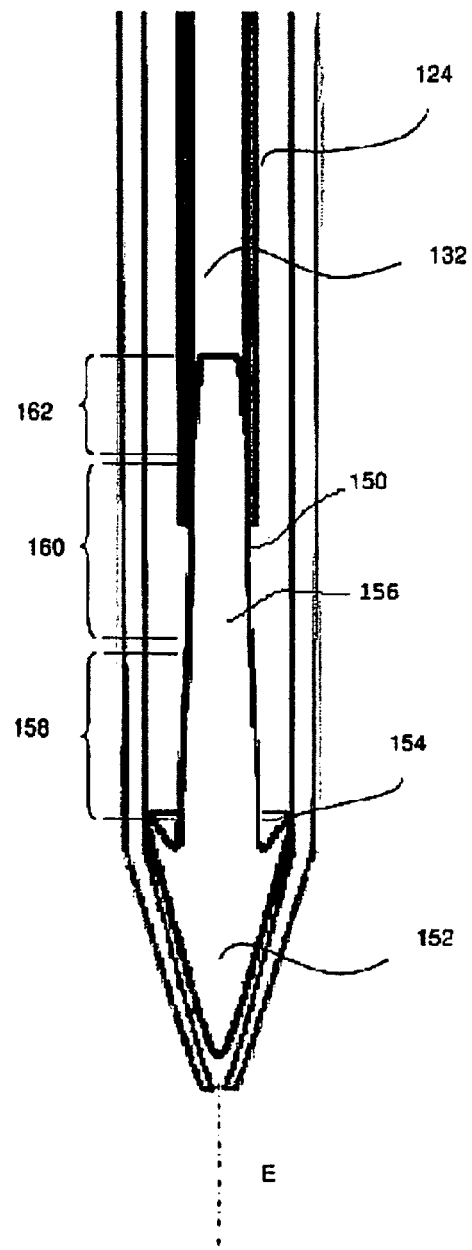
Fig. 5a
Fig. 5b

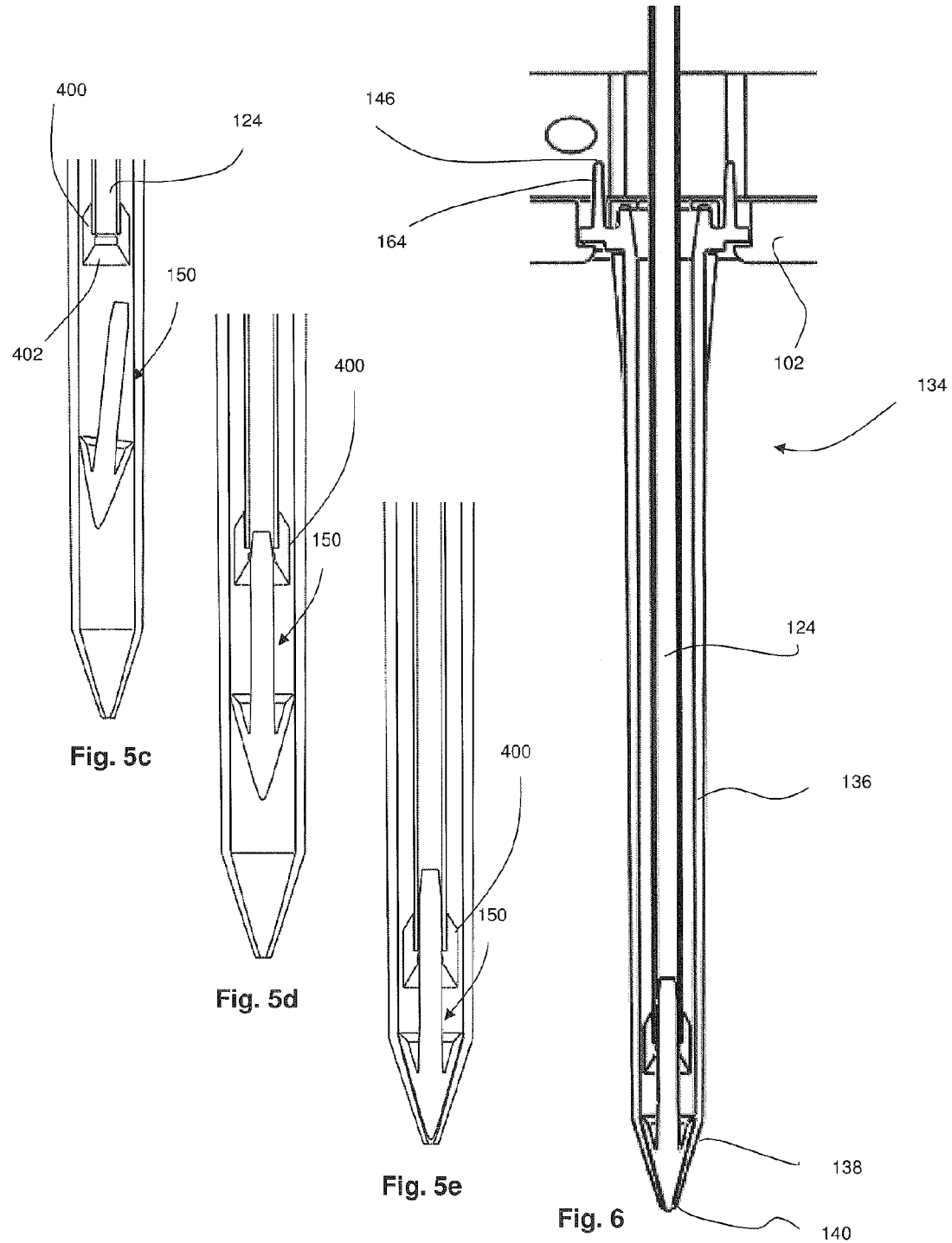

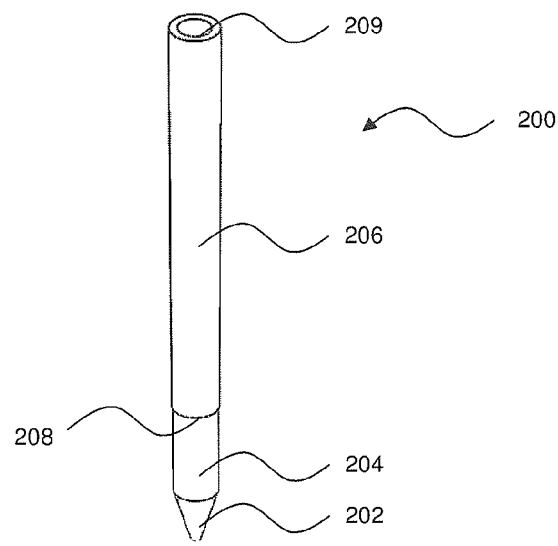
Fig. 12a
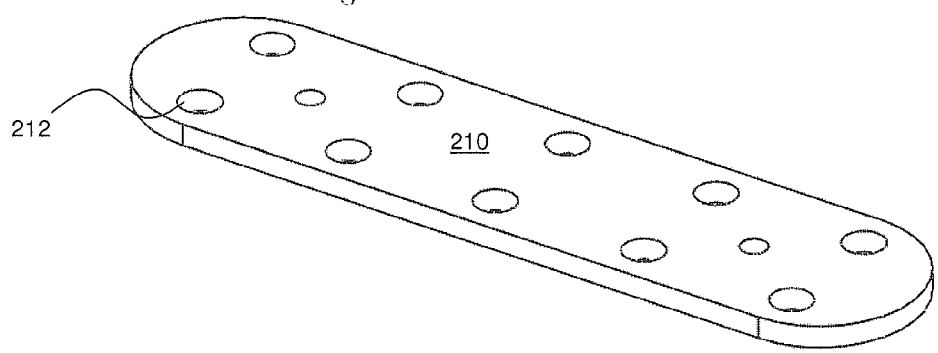
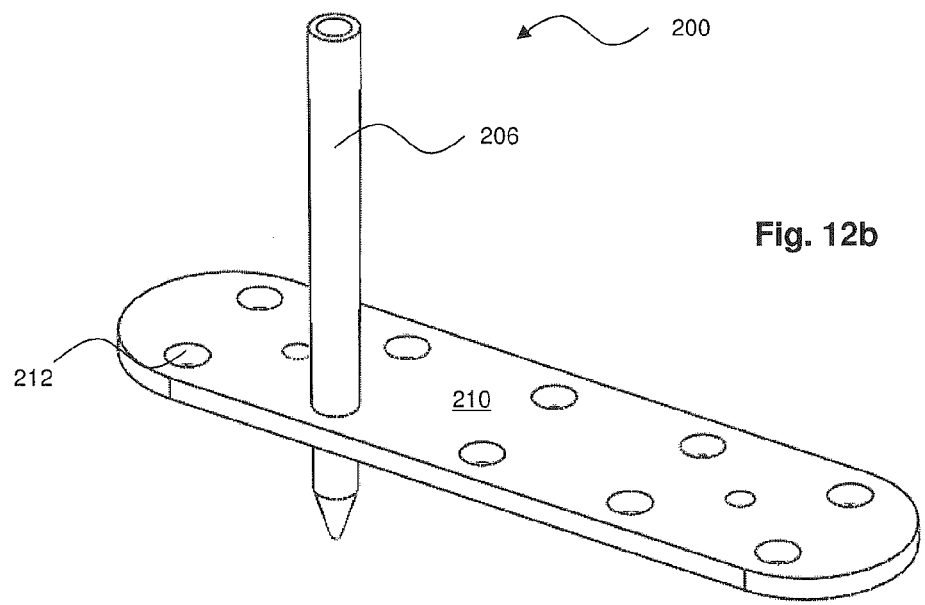
Fig. 12b

A B C D

A   B

C   D

LIQUID DISPENSING DEVICE

PRIORITY CLAIM

This application claims priority to British Application GB1213300.5, filed Jul. 26, 2012.

BACKGROUND

The present invention is concerned with a liquid dispensing device. More specifically, the present invention is concerned with a small volume droplet dispensing device, in particular for volumes in the order of 50 nanoliters to 100 microliters.

Within certain fields, such as protein crystallography, it is desirable to be able to dispense small volume samples, or droplets, of a given liquid. Such samples are dispensed at high speed into a well plate for subsequent analysis. A known droplet dispensing apparatus comprises a syringe defining a cylinder with a piston disposed therein. The liquid to be dispensed is stored within the cylinder and the piston is advanced in order to dispense controlled volumes of droplets.

Contact based dispensing systems are known in the art, in which a droplet is pushed from the syringe and put in contact with an external surface. The surface tension of the liquid allows the droplet to be dispensed by contact with the surface.

EP1344565 discloses a droplet dispensing apparatus in which a solenoid is used to "tap" the end of a piston rod and thereby advance a piston within a cylinder to dispense droplets of liquid. EP1344565 discloses an output member in the form of a drive rod attached to the solenoid which is spaced from a piston rod head attached to the piston rod. The solenoid accelerates the drive rod, which hits the head once the drive rod has built up speed, transferring momentum to the piston rod and liquid. The piston rod is connected to a striker, which striker is arranged to abut an adjustable anvil to arrest the movement of the piston rod. The mechanism facilitates droplet dispensing by suddenly stopping the piston and allowing a drop of liquid to be ejected under its own momentum.

The velocity of the droplet means it is "fired" from the syringe and does not require contact with a surface to be dispensed.

There are various problems with this approach. The collision due to this type of tapping motion causes shockwaves in the liquid which can cause dispensing problems. These problems include the dispensing of satellite droplets, as well as ingress of air into the syringe, both of which are undesirable. The shockwaves are caused by the collision between the moving drive rod and the stationary piston rod head (i.e. as a result of the gap between the drive rod and the piston rod head).

It is desirable to use removable/replaceable syringes for this type of apparatus. This prevents contamination, and allows different syringes to be used as the user requires.

A problem with the prior art is that when attaching a new syringe, the piston rod of the dispensing apparatus needs to be manually attached to the syringe piston. This can be labour intensive and time consuming.

Similarly, at the end of the dispensing operation, the syringes need to be separate from the piston rods in order to replace or clean them for re-use. Such removal can be time consuming.

A further problem with dispensing of liquids in this manner is splashing. Typically, a well-plate is provided in which several wells are formed to receive the dispensed liquids. Should any of the liquids splash from the wells it may enter adjacent wells or simply rest on top of the well plate. Both of these outcomes are undesirable.

SUMMARY

It is an aim of the present invention to overcome or at least mitigate one or more of the above referenced problems.

According to a first aspect of the invention, there is provided a droplet dispensing apparatus comprising:
a piston rod for connection to a piston of a droplet dispensing syringe,
a driver comprising a solenoid and an output member, the output member arranged to be accelerated by the solenoid,
in which the output member is configured to be in contact with the piston rod such that the output member and piston rod simultaneously accelerate from a stationary condition.

Advantageously, the provision of a connected output member and rod means that the piston experiences the full acceleration from a stationary condition to the maximum speed. In other words, the piston is accelerated with the driver as opposed to being "tapped" or struck once the driver is at speed (as with the prior art). It has been found that this method of dispensing is advantageous as it reduces the shockwave effect of the prior art; i.e., the piston is accelerated more gradually rather than being struck to accelerate it. Further, use of a solenoid in combination with this type of connection is advantageous for the following reasons. Once the solenoid has been actuated to push the piston rod, it is desirable to reset the system for a further dispensing operation. This involved moving the solenoid coil relative to the armature whilst keeping the piston rod stationary. Solenoids are especially well suited to this application because the armature can move relatively freely within the coil when the coil is not energised—i.e. the solenoid is an actuator having a "free" state where the output member can move freely and an "energised" state where the output member is urged in a downward direction.

Preferably the output member and the piston rod are attached—in other words they are fastened together to inhibit relative axial movement. They may be releasably attached to allow dis- and re-assembly.

Preferably the piston rod is connected to a striker, which striker is arranged to abut an anvil during the motion to arrest movement of the piston rod. This encourages dispense of the droplet by suddenly stopping the piston and allowing a drop of liquid to be ejected under its own momentum.

Preferably the apparatus comprises:
a base having a syringe receiving formation; and
a dispensing subassembly comprising the piston rod and driver,
in which the dispensing subassembly is movably mounted to the base.

This permits reset of the apparatus for a second dispense operation. Movement of the dispensing subassembly can move the solenoid housing and coil relative to the armature (which is held in place by the friction of the syringe piston in the syringe cylinder) to provide a further gap between the striker and anvil.

Preferably the dispensing subassembly is mounted on a bracket, which bracket is mounted to the base via a ballscrew actuator. Ballscrews allow high accuracy positioning and a high gear ratio suitable for a small electric motor to power the system. Back-driving is also difficult meaning the solenoid cannot back-drive the ball screw.

Preferably the piston rod is mounted for axial movement within a linear ball bearing arrangement. Advantageously, linear ball bearings offer low friction axial movement, which allows more accurate positioning of the rod.

According to a second aspect of the invention there is provided a method of operating a droplet dispensing apparatus comprising the steps of:

providing a driver comprising a solenoid and an output member, providing a piston rod, connecting the piston rod to a piston of a droplet dispensing syringe, simultaneously accelerating the output member and piston rod from a stationary condition whilst the output member and piston rod are in contact to advance the piston in the syringe to dispense fluid therefrom.

Preferably the piston rod is attached to the output member.

Preferably the method comprises the steps of:

providing a striker attached to the piston rod, providing an anvil, arresting movement of the piston rod by impact with the anvil.

According to a third aspect of the invention there is provided a droplet dispensing apparatus comprising:

a base defining a syringe attachment formation, a piston rod movably mounted to the base, an actuator arranged to move the piston rod, and, a syringe comprising a cylinder and a piston, in which the piston rod and the piston define complementary attachment formations configured to releasably join the piston rod and piston when driven together by the actuator whilst the syringe is held by the syringe attachment formation.

Advantageously, using the present invention, the syringe is inserted in the apparatus and the driver driven to pick up the piston. This eliminates the need for manual intervention (apart from attaching the syringe to the attachment formation), speeding up the syringe mounting process.

Preferably the complementary attachment formations are male and female formations. More preferably the male formation comprises a tapered formation becoming progressively wider with insertion into the female formation. This encourages alignment.

Preferably the male formation comprises a cylindrical formation extending from the large end of the tapered formation. The cylindrical formation ensures a secure axial fit, and alignment between the piston rod and piston. Any inaccuracies in component dimensions and positioning are thereby mitigated. The cylindrical formation also provides a large contact area between the components. Preferably the male formation comprises a further tapered formation extending from the cylindrical formation. This prevents over-insertion of the male formation. Preferably the male formation is defined on the piston, and the female formation defined on the piston rod.

Preferably the piston comprises a piston head, and a shaft extending therefrom comprising the male formation, in which the shaft is a stub shaft fully enclosed in the cylinder when the piston is in a fully advanced position. This allows for a compact syringe.

According to a fourth aspect of the invention there is provided a method of mounting a piston of a syringe to a droplet dispensing apparatus comprising the steps of:

providing a base of the apparatus defining a syringe attachment formation;

providing a piston rod of the apparatus movably mounted to the base, the piston rod comprising a first complementary attachment formation;

providing a syringe comprising a cylinder and a piston, the piston comprising a second complementary attachment formation;

attaching the cylinder to the syringe attachment formation;

driving the piston rod towards the piston to engage the complementary attachment formations.

According to a fifth aspect of the invention there is provided a syringe for a droplet dispensing apparatus comprising:

a cylinder; and, a piston, in which the piston defines a head and a shaft, the shaft having a tapered portion proximate a free end.

This arrangement is suited for use with an apparatus according to the third aspect. Preferably there is provided a cylindrical portion between the tapered portion and the head. The cylindrical portion ensures that the piston shaft and a piston rod having a female formation can engage at a plurality of positions along the length of the shaft. Also, the provision of a cylindrical portion means that the piston rod and piston shaft do not rotate relative to one another when attached, as they may do if the male formation was purely conical, and the female formation cylindrical. The cylindrical formation also provides a large contact area between the components once engaged.

More preferably there is provided a further tapered portion between the cylindrical portion and the head. Preferably the shaft is a stub shaft fully enclosed in the cylinder when the piston is in a fully advanced position.

According to a sixth aspect of the invention, there is provided a droplet dispensing apparatus comprising:

a base defining a syringe attachment formation and a stripping formation, a piston rod movably mounted to the base, an actuator arranged to move the piston rod, and, a syringe comprising a cylinder and a piston, the piston engaged with the piston rod, in which the actuator is configured to move the piston rod to pull the piston at least partially through the stripping formation to thereby separate the piston rod and piston.

Advantageously, using the present invention, the pistons can be stripped from the driving rods. This allows easy, quick and simultaneous removal of the syringes from the apparatus.

Preferably the piston and piston rod are engaged via an interference fit. This allows them to be simply pulled apart.

Preferably the stripping formation comprises an orifice, and the piston comprises a piston head, and the orifice is smaller in diameter than the piston head. This allows even force to be applied to the head to strip it from the rod without applying a bending load.

According to a seventh aspect of the invention there is provided a method of removing a piston of a syringe from a droplet dispensing apparatus comprising the steps of:

providing a base of the apparatus defining a syringe stripping formation;

providing a piston rod of the apparatus movably mounted to the base;

providing a syringe comprising a cylinder and a piston, the cylinder attached to the base and the piston being releasably attached to the piston rod, attaching the cylinder of the syringe attachment formation;

retracting the piston rod through the stripping formation to strip the piston from the piston rod.

According to a eighth aspect of the invention, there is provided a method of dispensing droplets of liquid, comprising the steps of:

providing a syringe having a piston disposed within a cylinder, the cylinder having an orifice, providing a liquid to be dispensed within the cylinder, moving the piston in a first direction to create a concave liquid surface at the orifice, moving the piston in a second direction, opposite to the first direction, to dispense a drop of liquid.

Advantageously, the "suck back" method described above, allows a smaller droplet to be dispensed at the same speed. Preferably the piston is accelerated in the second direction such that air is ejected at a first range of velocities, and liquid is ejected at a second, higher range of velocities. Because the initial acceleration (i.e. low speeds) ejects air, by the time the liquid is ejected the piston has reached much higher speeds, more suitable for droplet dispensing.

According to a ninth aspect of the present invention there is provided a well plate for receiving liquid samples comprising:

a body having a surface defining plurality of primary wells; and, a mask having a plurality of apertures formed therein, in which the mask is positioned on the surface to allow passage of fluids through the apertures into the primary wells.

Advantageously, the provision of a mask reduces the negative effects of splashing, i.e., any splashes will not sit on the well-plate itself, and will not be able to enter any adjacent masked wells.

Preferably the body has a surface defining a plurality of sub-wells, and which mask is configured to mask at least some of the sub-wells. Preferably the apertures are smaller than the mouths of the primary wells.

According to a tenth aspect of the present invention, there is provided a droplet dispensing apparatus comprising:

a piston rod for releasable connection to a piston of a droplet dispensing syringe;

a driver for advancing the piston rod; and, a syringe attachment formation having an interlock configured to at least partially inhibit movement of the piston rod when a syringe is not present in the attachment formation.

Advantageously, the presence of an interlock with respect to the syringe will inhibit the movement of the rod. Because of the force associated with the joining of the rod and the piston, it will be undesirable to have the rod extend from the apparatus without a syringe body in place as this may cause injury.

Preferably the interlock comprises a switch arranged to be actuated by a syringe within the syringe attachment formation.

Preferably the syringe attachment formation comprises a formation for receiving a projection of a syringe inserted therein, the interlock arranged to detect the presence of the projection.

According to an eleventh aspect of the invention, there is provided a droplet dispensing apparatus comprising a plurality of dispensing heads configured for dispensing controlled volumes of a liquid, in which the dispensing heads are arranged in at least two parallel rows.

Advantageously, this lowers the frequency of redundancy seen with prior art devices, which in turn reduces cycle time.

Preferably the dispensing heads are arranged in a matrix formation. More preferably each row comprises at least 5 dispensing heads.

The apparatus may comprise a well plate having matrix of 8 rows of 12 primary wells.

Preferably the dispensing heads are spaced within each row so as to dispense into non-adjacent primary wells.

According to a twelfth aspect of the present invention there is provided a method of dispensing droplets into a well plate, comprising the steps of:

providing a well plate having a matrix of primary wells, providing a droplet dispensing apparatus having a plurality of dispensing heads arranged in at least two parallel rows, using the droplet dispensing apparatus to simultaneously dispense liquid into multiple wells in at least two rows of the well plate.

Preferably the dispensing heads comprise syringes containing at least two different liquids; and, the step of using the droplet dispensing apparatus comprises the step of creating two differing volume gradients of each of the two liquids.

BRIEF DESCRIPTION OF THE DRAWINGS

An exemplary droplet dispensing apparatus, method of dispensing droplets and well plate will now be described with reference to the accompanying drawings in which:

FIG. 5a is a side section detail view of a further part of the apparatus of FIG. 1;

FIG. 5b is a side section detail view of a part of the apparatus as shown in FIG. 1;

FIG. 5c is a side section detail view of an alternative arrangement to that of FIG. 5b;

FIG. 5d is a side section detail view of the arrangement of FIG. 5b in a second stage of operation;

FIG. 5e is a side section detail view of the arrangement of FIG. 5b in a third stage of operation;

FIG. 6 is a side section detail view of a part of the apparatus of FIG. 1;

FIG. 12a is a perspective view of a part of a second droplet dispensing apparatus in accordance with the present invention;

FIG. 12b is a further perspective view of the part of the second droplet dispensing apparatus of FIG. 12a;

DETAILED DESCRIPTION

Figure 1:
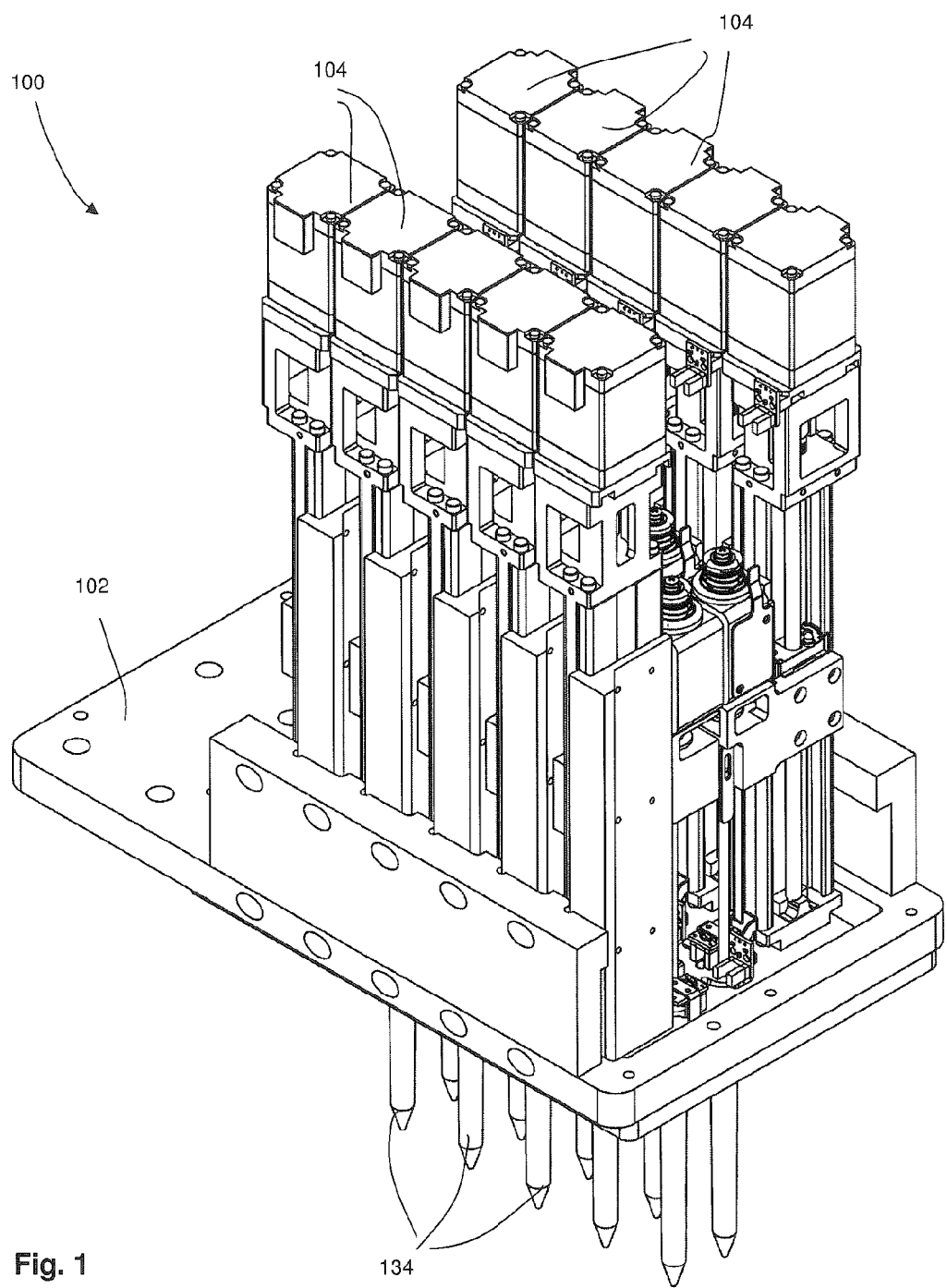
FIG. 1 is a perspective view of a first droplet dispensing apparatus in accordance with the present invention.

Referring to FIG. 1, a droplet dispensing apparatus 100 is shown, comprising a base plate 102 on which ten individual droplet dispensing modules 104 are installed. The modules 104 are arranged in two adjacent rows of five modules 104 as shown.

Each of the modules 104 is identical and, as such, only one module will be described in detail.

Figure 2:
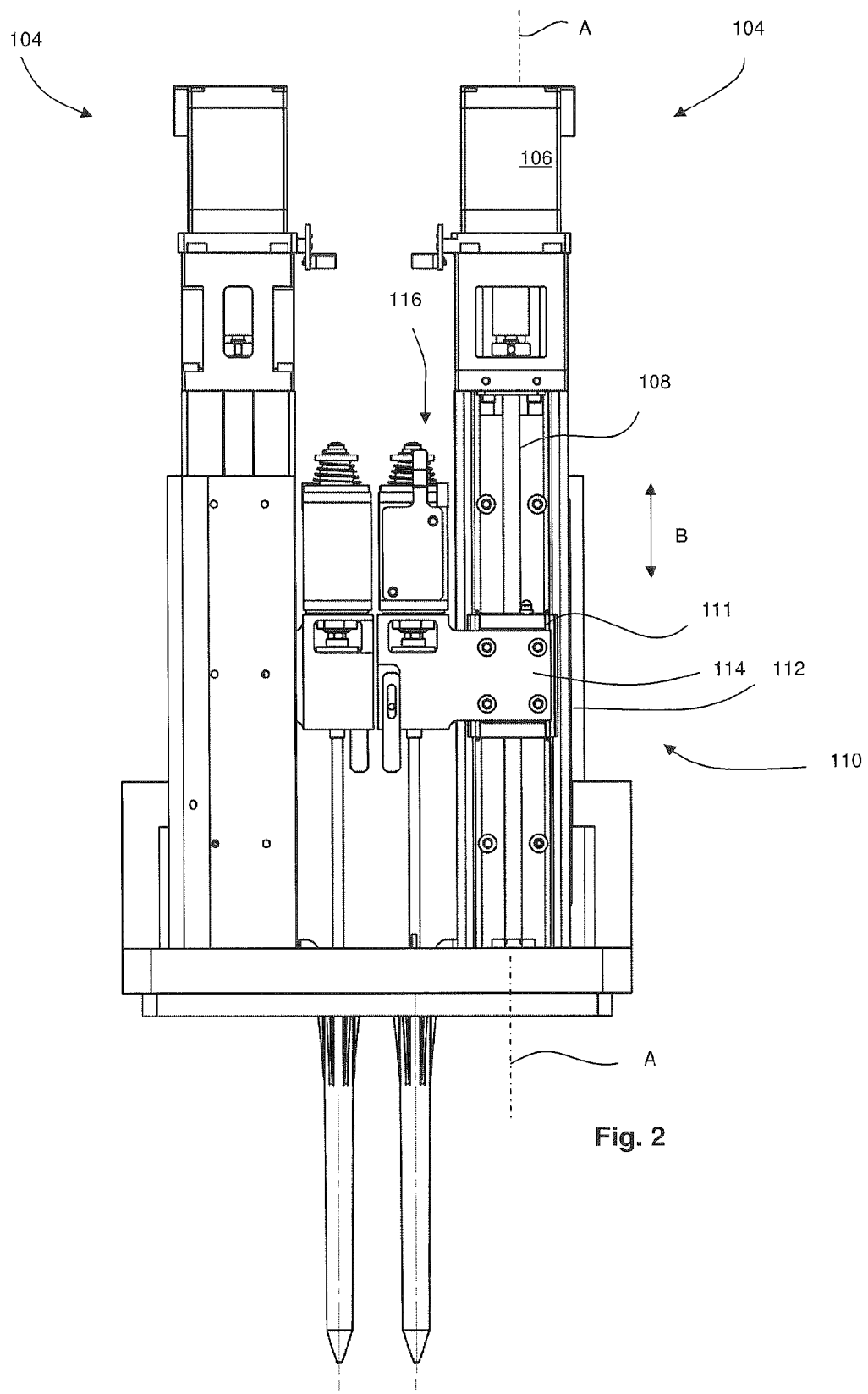
FIG. 2 is a side view of the apparatus of FIG. 1.
Figure 3:
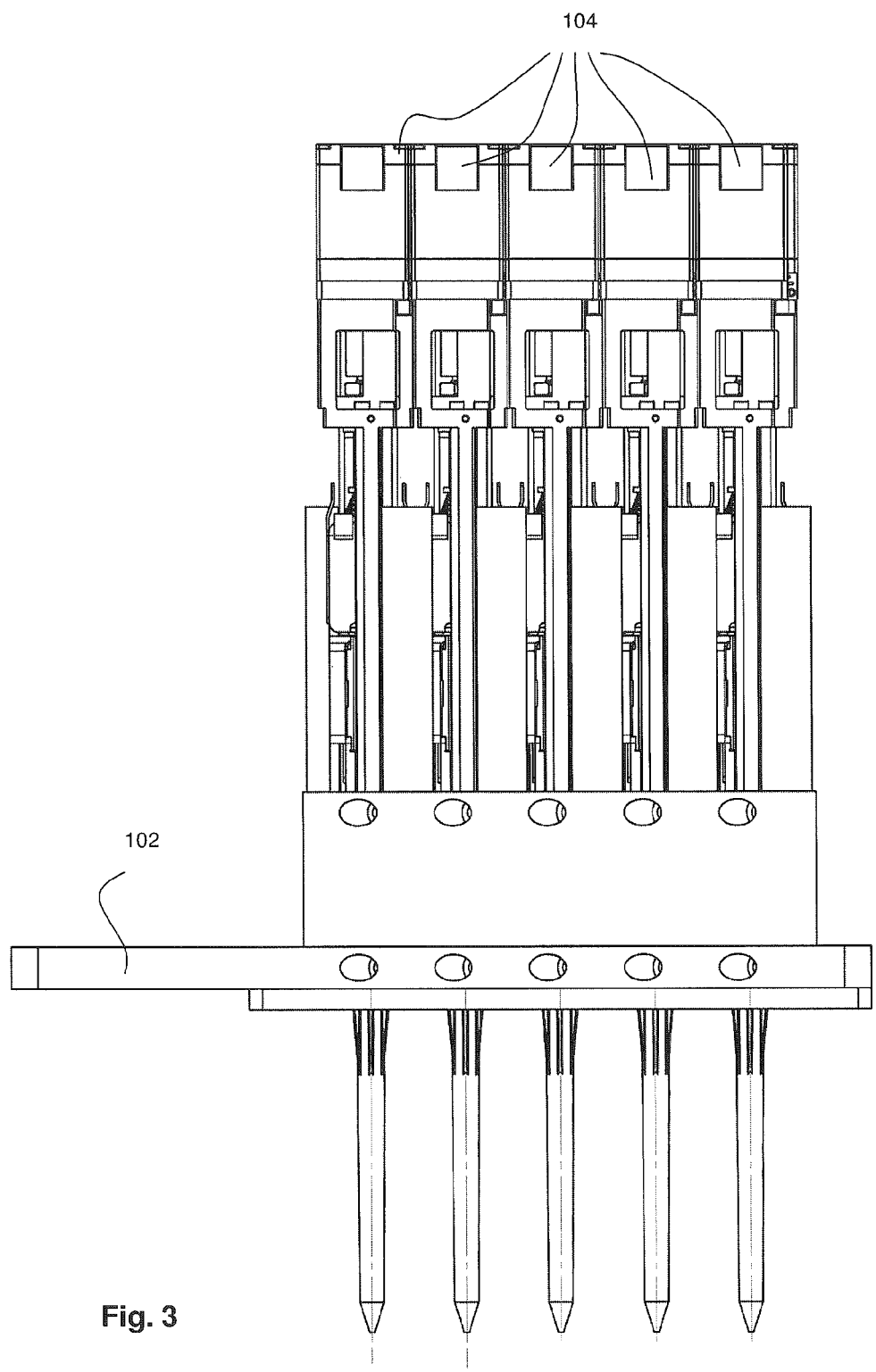
FIG. 3 is a front view of the apparatus of FIG. 1.

Referring to FIG. 2, two modules 104 can be seen. Each module 104 comprises a vertically oriented motor 106 being arranged to drive a vertically oriented threaded ball screw shaft 108 (the thread is not shown). The shaft 108 is mounted for rotation about a vertical axis A in two bearings, one at either end (not visible). A ball screw nut assembly 110 is mounted on the ball screw shaft 108 and is constrained against rotation about the axis A by a slide frame 112. The assembly 110 comprises a ball screw nut 111 engaged with the shaft 108. Ball screw nuts in general are known in the art, and as such will not be described in detail here. As such, rotation of the shaft 108 about the axis A will result in movement of the nut assembly 110 in a vertical direction along axis A as indicated by arrow B.

Attached to the nut assembly 110 there is provided a bracket 114. The bracket 114 is mounted to the nut assembly 110 for movement therewith.

The bracket 114 is configured to hold a dispensing sub-assembly 116 which will be described further below.

The dispensing sub assembly 116 comprises a solenoid actuator 118 connected to the bracket 114 and mounted vertically so as to define a solenoid axis C, offset from the axis A of the ball screw. The solenoid actuator 118 comprises an output shaft 122 which is arranged to move along the axis C in a vertical direction D. The output shaft 122 is connected to a piston rod 124 which is slidably mounted in a linear ball bearing 126 for movement along the axis C. The use of a linear ball bearing 126 is important, as its low friction allows for very accurate linear positioning of the piston rod 124. The piston rod is constructed from a metal material. The linear ball bearing keeps the piston rod 124 straight. At the top end of the piston rod 124, and attached thereto, there is provided an annular collar forming a piston striker 128. An annular anvil 130 provided, and is attached to the bracket 114. The piston rod 124 passes through the anvil 130 such that downward motion of the striker 128 is limited by the piston striker 128 when it strikes the top surface of the anvil 130.

Turning to FIG. 5b, a lower part of the piston rod 124 opposite the striker 128 is shown in cross section. As can be seen, the piston rod 124 has an axial bore 132 defined therein and is open at its lower, free end.

The lower end of the piston rod 124 projects through the base plate 102 (through a bore) to an underside of the base plate 102.

The apparatus 100 further comprises a plurality of syringes 134, each of which has a generally cylindrical body 136, having at a first end a conical tip 138 ending in a droplet dispensing orifice 140. The body is constructed from polypropylene (PP). At the opposite end of the body 136 to the top 138 there is provided an attachment formation 142 comprising a flange 144 having a pair of pins 146 projecting therefrom, in the opposite direction to the body 136. The pins 146 extend substantially parallel, but offset from, a main axis E of the syringe 134. The attachment between the flange 144 and the body 136 is facilitated by a number of stiffening ribs 148.

Within the body 136 there is provided an axially slidable piston 150, constructed from polyethylene (PE). The piston 150 comprises a head 152 which is generally conical, having a similar outer profile to the inner profile of the tip 138 of the body 136. The head 152 has an annular recess 154 at the axial face of its wider end, the annular recess 154 surrounding a stub shaft 156 projecting axially therefrom along the axis E.

The stub shaft 156 comprises a first tapered portion 158 which tapers inwardly to make the shaft thinner as it moves away from the head 152. The shaft then defines a cylindrical portion 160 before terminating in a second tapered portion 162 at the end opposite the head 152.

It will be noted that the widest portion of the head 152 proximate the annular recess 154 forms a tight seal with the inside diameter of the cylinder. The annular recess 154 allows the outer periphery of the head to flex and seal against the body 136.

The syringe 134 is provided as shown in FIG. 5a, i.e., with the piston 150 engaged at the lower end proximate the orifice 140. To install the syringe, the piston rod 124 is retracted and the flange 144 is engaged with a syringe receiving formation on the underside of the base plate 102 as shown in FIG. 6. In this embodiment, the syringe is attached with a twist lock formation, although variations are possible as will be described below. Each of the pins 146 enters a respective orifice 164 on the underside of the base plate 102 and detection means are provided such that the presence of the syringe 134 can be confirmed.

Once the presence of the syringe 134 has been confirmed, the piston rod 124 is driven downwards by running the motor 106 which moves the bracket 114 downwards towards the syringe. As such, the piston rod 124 is pushed into the cylinder 136. As this occurs, the open end of the rod 124, as shown in FIG. 5b, engages the tapered second portion 162 of the piston 150 and these two components mate. As the tapered portion 162 expands, the fit between the rod 124 and the piston 150 becomes firmer and eventually the two are engaged via an interference fit at the cylindrical section 160.

The piston rod is not driven all the way to the head 152 (as shown in FIG. 5b) such that some degree of bending flexibility remains between the piston rod 124 and piston 150. This allows the piston 150 to move and better seal against the inside of the body 136. The piston shaft is more flexible than the piston rod, because the former is constructed from a plastics material (polyethylene) as opposed to the metal rod.

In an alternative arrangement shown in FIGS. 5c to 5e, a guide component 400 is provided at the end of the piston rod 124. The guide component is generally annular and defines a central axial bore in which the piston rod 124 fits. The fit is an interference fit. The component 400 is of a larger outer diameter than the piston rod 124, but smaller in diameter than the inside of the syringe cylinder body.

Facing away from the piston rod 124, the component 400 defines a concave chamfered portion 402. The chamfer acts to guide the piston 150 into the bore of the component, which leads into the bore of the piston rod 124, as shown in FIGS. 5c to 5e. The component 400 fits to the outside surface of the piston rod 124, and as such acts as a guide only and does not affect the fit between the piston rod and piston.

Figure 7:
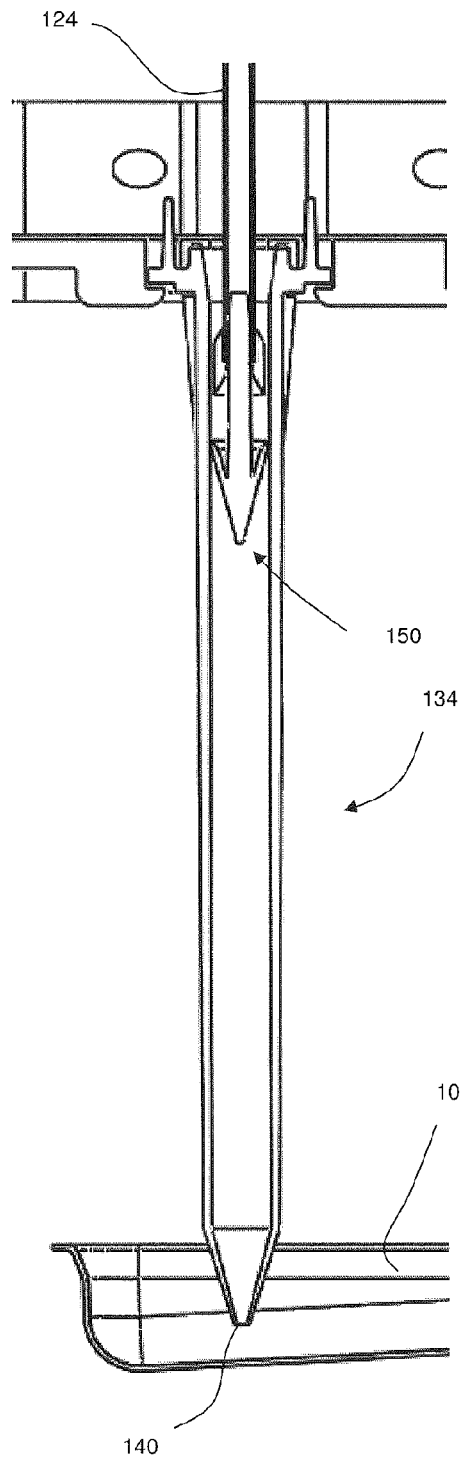
FIG. 7 is a view similar to FIG. 6 in a different configuration.

Once the piston 150 has been secured to the piston rod 124 (see FIG. 6), it can be withdrawn with the orifice 140 of the syringe 134 immersed in a fluid 10, as shown in FIG. 7. The required volume of liquid can then be aspirated whilst the ball screw retracts the piston rod 124. Once the desired volume has been aspirated, the system is ready to dispense.

Figure 4:
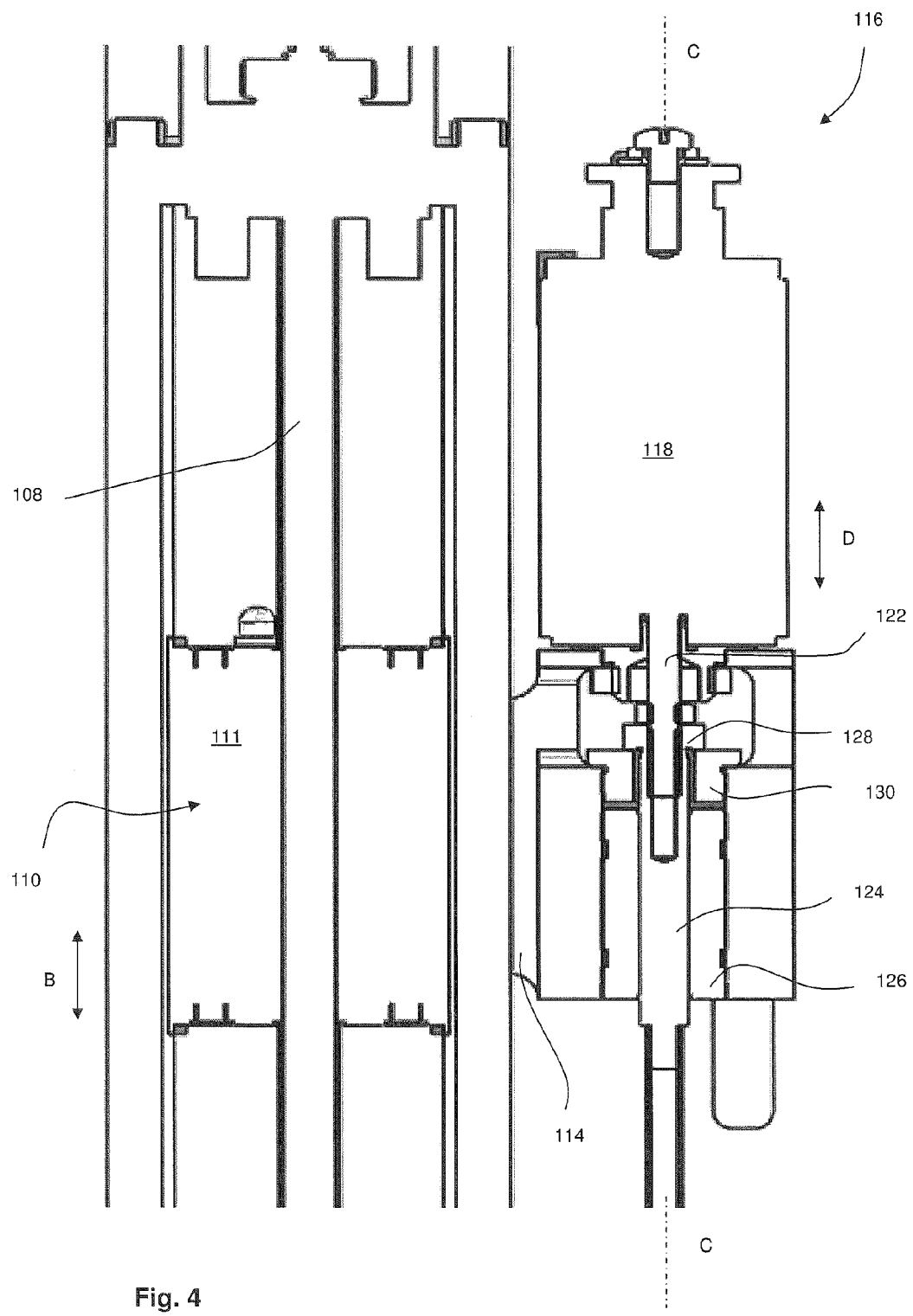
FIG. 4 is a side section view of a first part of the apparatus of FIG. 1.
Figure 10A:
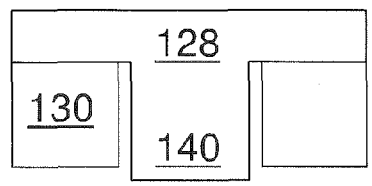
FIGS. 10a to 10c are schematic views of a part of the apparatus of FIG. 1 showing a first operating sequence.
Figure 10B:
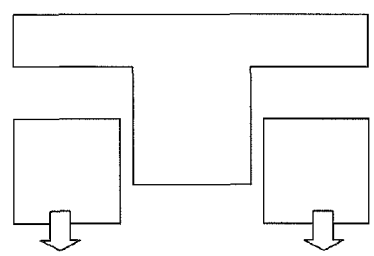
Figure 10C:
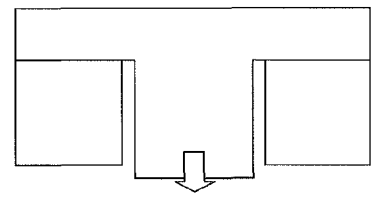

Turning back to FIG. 4, droplets can be dispensed from the orifice 140 by actuating the solenoid 118 to move the output shaft 112 in a downwards direction. The sequence of events is shown in FIGS. 10a to 10c. In FIG. 10a, the piston rod 140 is static with the striker 128 resting on the anvil 130. At this point, the ballscrew is turned to advance the subassembly towards the syringe. This lowers the anvil 130, and moves it away from the striker as shown in FIG. 10b. Once the gap between the striker 128 and the anvil 130 corresponds to the amount of piston travel required to dispense the desired amount of liquid, the solenoid pushes the piston rod 140 such that the striker 128 hits the anvil 130 as shown in FIG. 10c.

The piston head 152 is attached to the rod 124, and a direct, uninterrupted load path from the solenoid to the piston head 152 is present throughout the entire acceleration (i.e. from zero to full speed to zero). Because of this, the piston head 152 is initially accelerated smoothly without the impulse "shock" present in the prior art.

As the piston striker 128 strikes the anvil 130, movement is arrested, and the momentum of the liquid carries it from the orifice.

In order to produce another shot, the ball screw shaft 108 is rotated. As this occurs, the bracket 114 is lowered. The fit between the piston 150 and the cylinder 136, and the consequent resistance to movement is such that the piston rod 124 does not move (the static friction is not overcome by the applied force). As such, the solenoid armature will simply move back within the solenoid as this occurs. During this motion, the piston striker 128 is lifted away from the anvil 130. Once the desired stroke distance has been met, the shaft 128 is stopped and the solenoid actuator 118 can be powered in order to push the piston rod 124 down in order that the striker 128 strikes the anvil 130 and a further droplet is dispensed. The volume of droplet can be varied by varying the distance the ballscrew is moved.

The apparatus can then be moved, over a different set of wells, and further droplets dispensed.

Figure 9A:
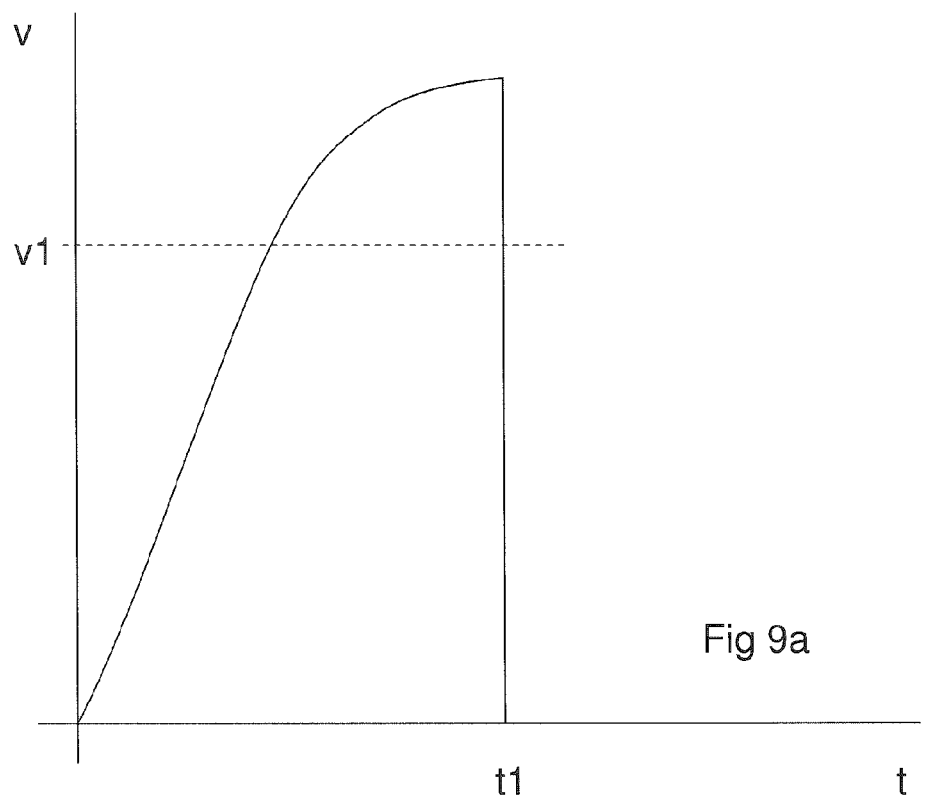
FIGS. 9a and 9b are velocity-time graphs for the syringe head of the present invention.
Figure 9B:
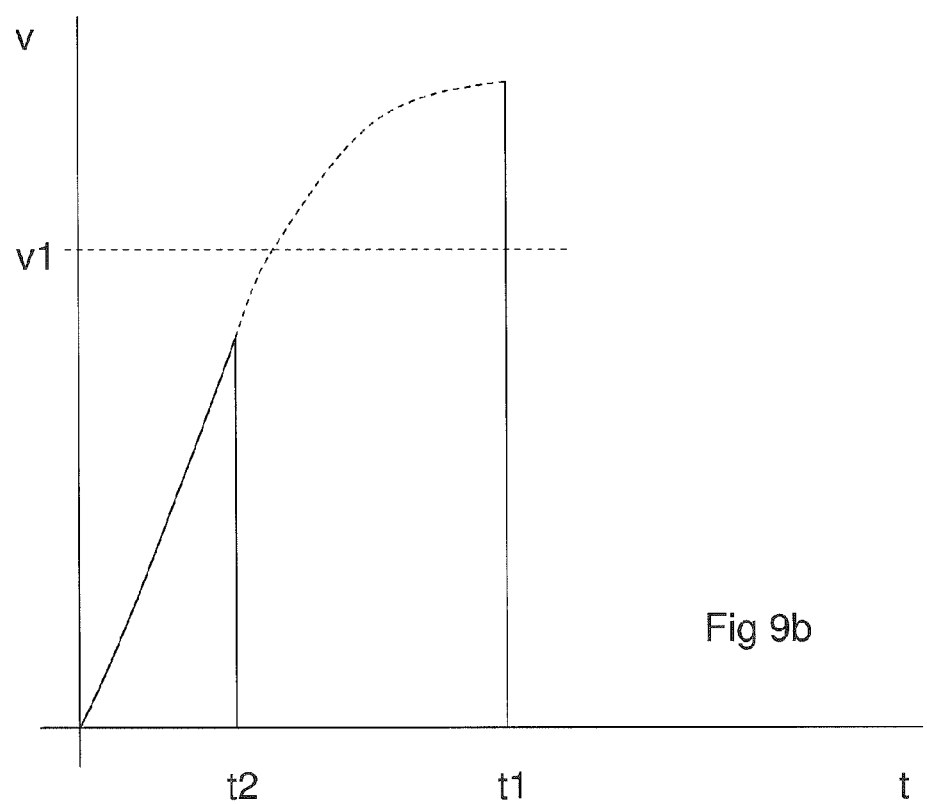

Turning to FIGS. 9a and 9b a typical velocity time graph for the solenoid 118 is shown. As can be seen, the solenoid 118 accelerates the piston rod 124 and pushes liquid from the syringe until the striker 128 hits the anvil 130 at time t1. It is known that in order to successfully dispense a droplet, the velocity of the piston should reach a sufficient value, e.g., v1 as shown in FIG. 9. Should a smaller droplet be dispensed this can be problematic as the stroke length is decreased (i.e. the ball screw shaft 108 is not rotated as much), and therefore the solenoid 118 does not have the time to get up to speed before the striker 128 hits the anvil 130. Therefore, as shown for example in FIG. 9b, at time t2, velocity v1 may not be reached. This can be problematic.

Figure 11A:
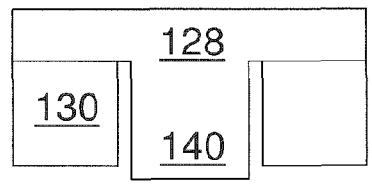
FIGS. 11a to 11d are schematic views of a part of the apparatus of FIG. 1 showing a second operating sequence.

According to the present invention, there is provided a method in which when a particularly small droplet is required (in the order of 50 nl). This sequence is shown in FIGS. 11a to 11d. FIG. 11a shows the starting position of the piston rod 140, with associated striker 128 resting against the anvil 130.

Figure 11B:
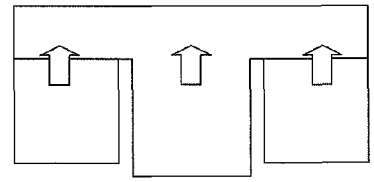
Figure 11C:
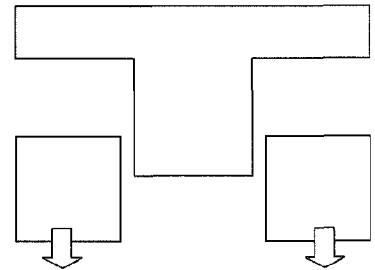

The motor 106 is used to first wind the shaft 108 in reverse. This raises the anvil 130 to raise the piston rod 140 as shown in FIG. 11b. Due to movement of the associated piston head 152, the meniscus of the fluid within the body 136 becomes concave at the orifice 140 and a small amount of air enters the body 136 (although not so much that a bubble is formed). The shaft 108 is then returned to its original position (the piston head 152 remains in position due to static friction with the body 136) and further advanced by an amount equivalent to the desired volume to be dispensed. This position is shown in FIG. 11c.

Figure 11D:
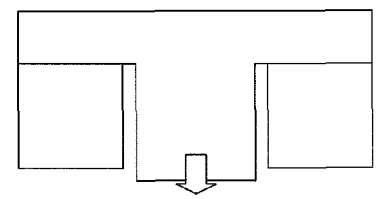

The forward stroke as shown in FIG. 11d can then be activated by the solenoid 118 which will initially eject the air formed by the concave meniscus followed by the liquid. Turning to FIG. 9b, the advantage of this method is that the output shaft 124 can accelerate to its full speed (i.e. exceeding V1) to dispense the liquid. Essentially, the first part of the motion is ejecting a small amount of air at a relatively low speed from the orifice 140. This allows a small volume of liquid to be dispensed at the appropriate speed. This method is intended where stroke distance is around 10 micrometers or less (the size of syringe will determine the volume to which this distance relates).

Once the correct amount of liquid has been dispensed, and the user wishes to finish the operation, the syringe 134 can be removed as follows.

Figure 8:
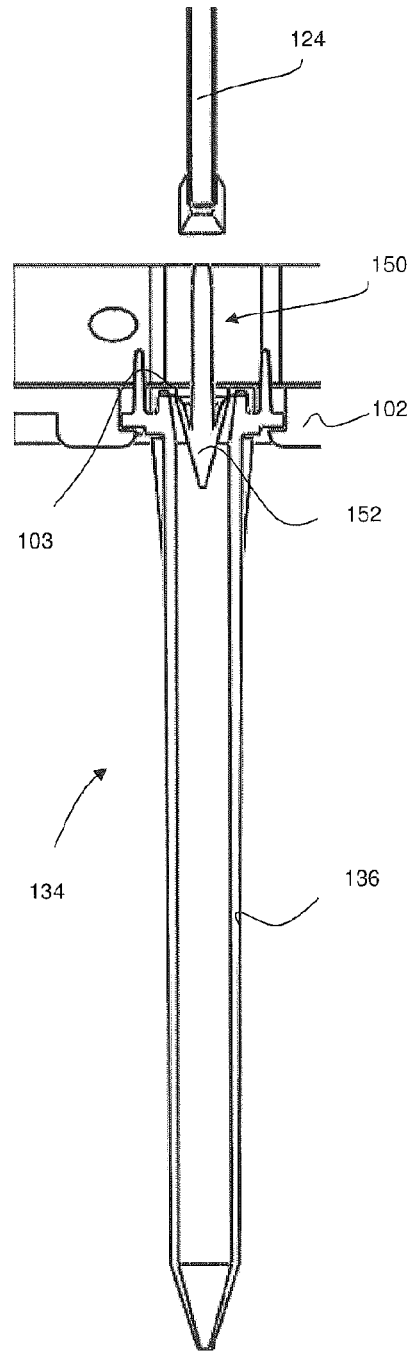
FIG. 8 is a view similar to FIG. 6 in a still different configuration.

Turning to FIG. 8, with the syringe 134 in place, the piston rod 124 is fully withdrawn. As the piston 150 reaches the top of the cylinder 136 the head 152 encounters the lower surface of the base plate 102. Because an orifice 103 in the base plate 102 is not large enough for the head 152 to pass, the head is stripped from the piston rod 124. The piston head 152 is retained in the cylinder 136. The syringe 134 is removed from the assembly, which is primed for a further piston to be installed.

Turning to FIGS. 12a and 12b, an alternative apparatus and method for mounting a series of syringes 200 to a droplet dispensing apparatus is shown. Instead of an attachment formation (such as a twist lock) being provided on the open end of the syringe, instead the syringe comprises a tip 202, a first cylindrical portion 204 and a second cylindrical portion 206 with a shoulder 208 therebetween.

A guide plate 210 is provided, and is arranged to be mounted underneath, parallel to, and offset from, the base of an appropriate droplet dispensing apparatus (e.g. base 102 of apparatus 100). The guide plate is generally flat and planar.

The guide plate 210 defines a series of through-bores 212 which reflect the desired arrangement of syringes for droplet dispensing. The guide plate 210 is removably mounted in the droplet dispensing apparatus so that it can be removed for the loading and unloading of syringes 200.

Once removed, the syringes 200 can be inserted into the bores 212 in the guide plate from above. The bores 212 have a diameter equal to or greater than the diameter of the first portion 204, but less than the diameter of the second portion 206, such that the shoulder 208 abuts the plate 210 and holds the syringe 200 in place. Unlike the first mentioned embodiment, the syringes can be top loaded into the plate 210 providing visibility of the mating structures. This is in contrast to the apparatus 100 in which the syringe head interface with the plate would not be readily visible.

The loaded plate 210 can then be placed into the apparatus and the various heads within the syringes 200 (not visible) can be picked up and actuated by the piston rods as described above. The loaded plate 210 is vertically actuable within the apparatus to clamp the syringe between the shoulder 208 and a top end 209 which abuts the underside of a base plate.

It is within the scope of the present invention that a detection/interlock system be partially located with the guide plate 210, to signal to the apparatus that all syringes have been inserted. This then allows the piston rods to actuate. The interlock system is provided with both a plate sensor (to ensure plate 210 is in position) and a set of syringe sensors within the plate 210.

Figure 13A:
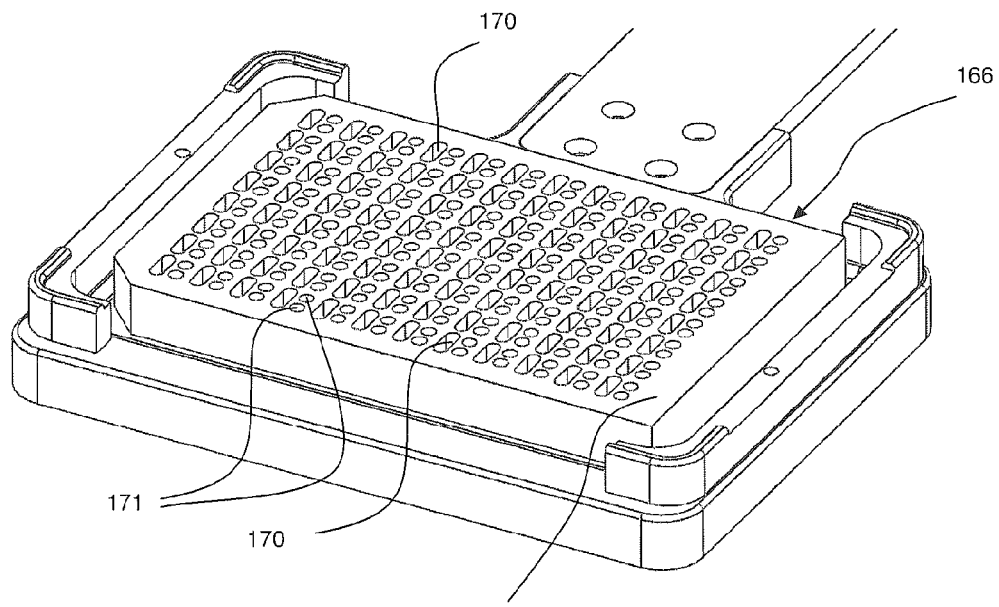
FIG. 13a is a perspective view of a well plate.

Turning to FIG. 13a, a well plate 166 is shown which is generally rectangular and comprises a top surface 168 defining a number of primary wells 170 and a pair of associated sub-wells 171 associated with each primary well. Typically, liquid will be dispensed into each of the primary wells by the dispensing apparatus.

Figure 13B:
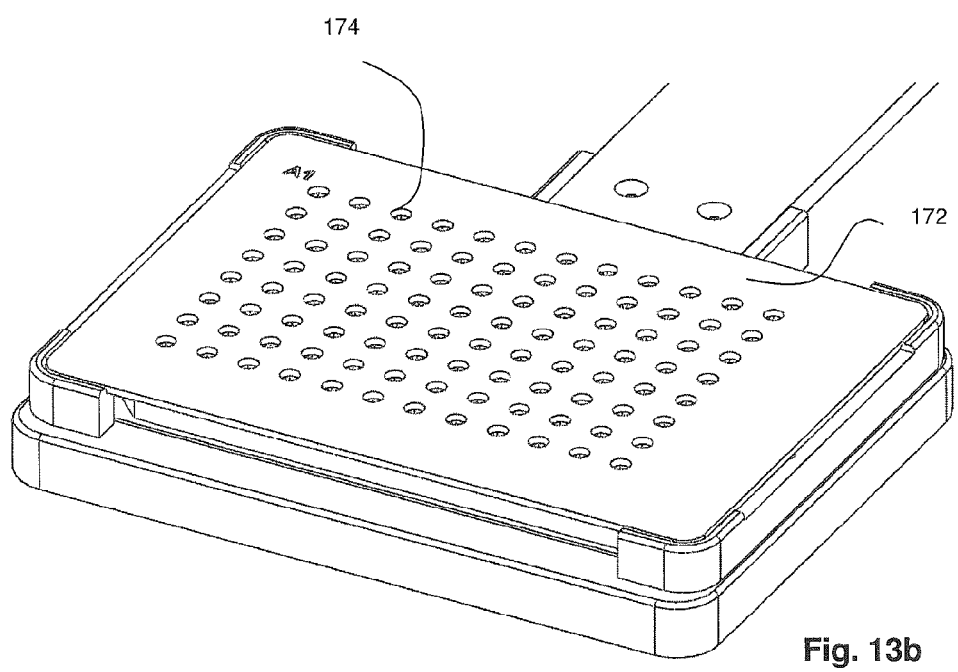
FIG. 13b is a perspective view of the well plate of FIG. 9 with a mask applied thereto in accordance with the present invention.

As described above, splashing can be a problem. Excess liquid can land in adjacent sub-wells 171, or alternatively can land on the top surface 168, which is also undesirable. As such, as shown in FIG. 13b, a mask 172 is provided in the form of a plate having a plurality of orifices 174. Each of the orifices 174 corresponds to a primary well 170. The orifices are smaller than the mouths of the wells 170 such that splashing is reduced. The mask also completely covers the mouths of the sub-wells 171. In fact, the orifices in the mask 174 are only as large as they need to be in order to receive a droplet from the dispensing syringe. Any excess splashing will occur on the mask rather than on the top surface 168 of the well plate 166.

Figure 14A:
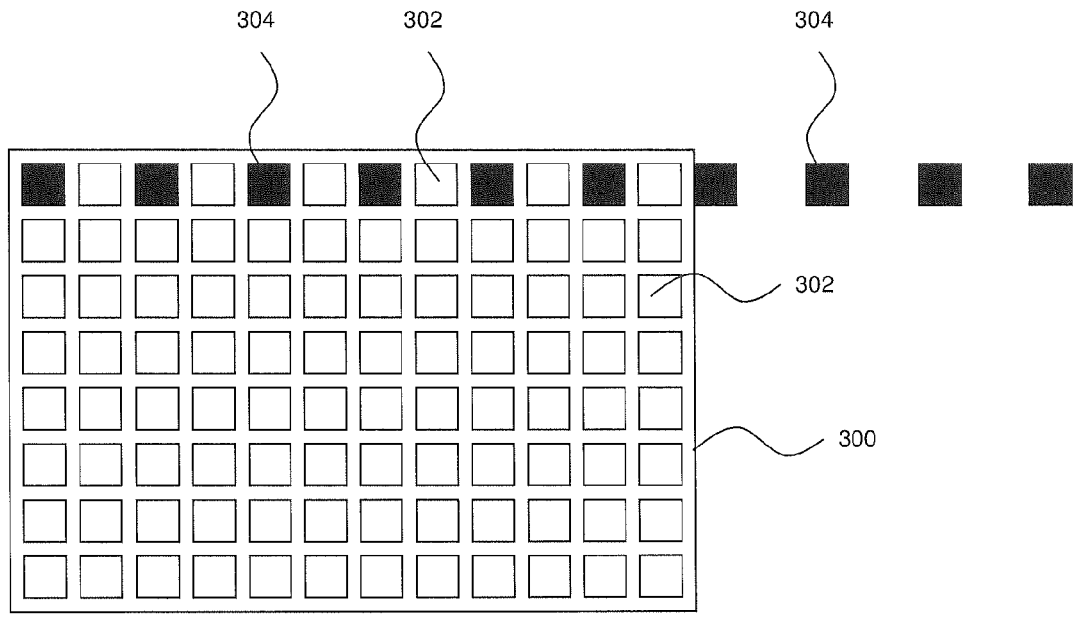
FIG. 14a is a plan view of a well plate being filled by a prior art dispensing apparatus.

Turning to FIG. 14a, traditionally, droplet dispensing apparatuses of the prior art have a single row of heads. A well plate 300 having a matrix of 12×8 primary wells 302 is shown, in which a single row of 10 heads 304 is provided. Ideally heads would be spaced to simultaneously dispense into adjacent wells, so that a maximum number of different dispenses could be done simultaneously for a given number of wells. This is not usually possible because of packaging constraints so the heads are pitched at multiples of the well-to-well pitch (for example every two or three wells). As can be seen, a maximum of 6 dispenses can be done in parallel with the configuration shown in FIG. 14a because the heads have to be spaced to dispense into alternate wells.

Figure 14B:
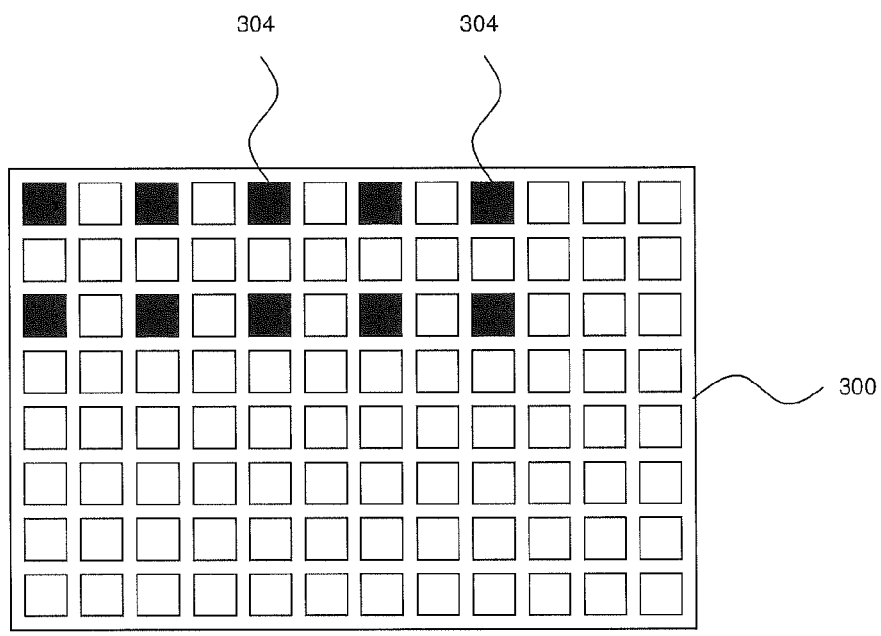
FIG. 14b is a plan view of a well plate being filled by a dispensing apparatus in accordance with the present invention.

Turning to the layout of FIG. 14b, the present invention provides 10 heads 306 in two rows of 5. This configuration means that up to 10 different dispenses can be performed in parallel in some cases this can reduce cycle time compared to the single row of 10 heads of FIG. 14a.

During many dispensing procedures, including protein crystallography, the wells need to be filled with varying amounts of fluids. Consider FIG. 14c, in which four syringes A, B, C, D in a known dispensing apparatus contain different fluids.

Figures 14C, 14D, 14E:
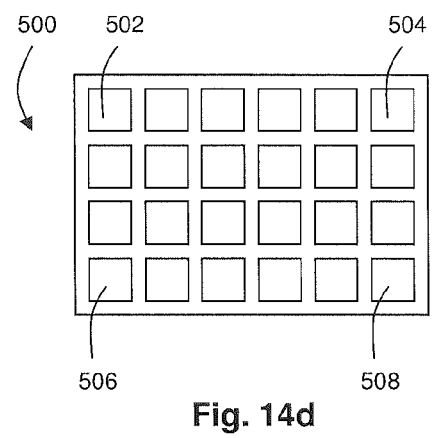
FIG. 14c is a plan view of an example known arrangement of syringes containing different liquids.
FIG. 14d is a plan view of a well plate.
FIG. 14e is a plan view of an arrangement of syringes containing different liquids in accordance with the present invention.

Consider also the well plate 500 of FIG. 14d having top left well 502, top right well 504, bottom left well 506 and bottom right well 508. According to the requirement of the experiment in question, liquid A must start with the highest volume in well 502, and then decreasing diagonally towards well 508. Similarly the highest volume of liquid B is required in well 504, decreasing diagonally towards well 506. The highest volume of liquid C is required in well 506, decreasing diagonally towards well 504, and the highest volume of liquid D is required in well 508, decreasing diagonally towards well 502.

FIG. 14e shows a dispensing arrangement according to the present invention. Using the arrangement of FIG. 14e will be faster than the arrangement of FIG. 14c because wells requiring similar dispense volumes are dispensed into more frequently than with the single row of FIG. 14c. In other words, the dispensing heads spend less time on average waiting for the slowest filling head to complete its dispense.

Variations fall within the scope of the present invention.

Instead of providing a series of modules 104 on a fixed, static, base 102, one or more modules 104 could be mounted on a base which forms part of a hand-held apparatus.

The invention claimed is:

1. A droplet dispensing apparatus for actuating a syringe to dispense droplets, comprising:
a syringe receiving formation,
a piston rod for connection to a piston of a droplet dispensing syringe, the piston rod being arranged to extend from the apparatus into the droplet dispensing syringe to connect to the piston,
a driver comprising a solenoid and an output member, the output member being fixedly attached to the solenoid and arranged to be accelerated by the solenoid towards a droplet dispensing orifice of the syringe,
a striker attached to the piston rod, and
an anvil arranged to arrest movement of the piston rod by impact of the striker on the anvil, and
wherein the output member is configured to be in contact with the piston rod such that the output member and piston rod simultaneously accelerate from a stationary condition.

2. The droplet dispensing apparatus according to claim 1 in which the output member and the piston rod are attached.

3. The droplet dispensing apparatus according to claim 1, in which the striker is arranged to abut the anvil during the impact to arrest movement of the piston rod.

4. The droplet dispensing apparatus according to claim 1 comprising:
a base having the syringe receiving formation formed thereon; and
a dispensing subassembly comprising the piston rod and the driver,
in which the dispensing subassembly is movably mounted to the base.

5. The droplet dispensing apparatus according to claim 4, further comprising:
an actuator comprising a ballscrew; and
a bracket mounted to the base via the actuator,
wherein the dispensing subassembly is mounted on the bracket.

6. The droplet dispensing apparatus according to claim 5, further comprising:
a motor;
wherein the ballscrew comprises a nut and a shaft, and the bracket is mounted on the nut of the ballscrew, and the shaft of the ballscrew is driven by the motor.

7. The droplet dispensing apparatus according to claim 1, further comprising a linear ball bearing arrangement, and the piston rod is mounted for axial movement within the linear ball bearing arrangement.

8. The droplet dispensing apparatus according to claim 4, further comprising:
a syringe comprising a cylinder and a piston,
wherein the piston rod and the piston define complementary attachment formations configured to releasably join the piston rod and piston and configured to be joined by being driven together by the actuator with the syringe being held by the syringe receiving formation.

9. The droplet dispensing apparatus according to claim 8 in which the complementary attachment formations are male and female formations, at least one of a male or female formation being provided on the piston rod and the other of a male or female formation being provided on the piston.

10. The droplet dispensing apparatus according to claim 9 in which the male formation comprises a tapered formation including a first insertion end and a second end, wherein the formation progressively widens from the first insertion end towards the second end.

11. The droplet dispensing apparatus according to claim 10 in which the male formation comprises a cylindrical formation extending from the second end of the tapered formation.

12. The droplet dispensing apparatus according to claim 11 in which the male formation comprises a further tapered formation extending from the cylindrical formation.

13. The droplet dispensing apparatus according to claim 9 in which the male formation is defined on the piston, and the female formation defined on the piston rod.

14. The droplet dispensing apparatus according to claim 13 in which the piston comprises a piston head, and a shaft extending therefrom comprising the male formation, in which the shaft is a stub shaft fully enclosed in the cylinder when the piston is in a fully advanced position.

15. A droplet dispensing apparatus, comprising:
a piston rod;
a syringe receiving portion;
a driver, comprising a solenoid and an output member adapted for contact with the piston rod, the output member being fixedly attached to the solenoid and arranged to be accelerated by the solenoid toward an output direction of the syringe receiving portion;
an anvil; and
a striker;
the striker being attached to the piston rod and the anvil being arranged to limit travel of the striker in a first direction, the anvil being movable in a second direction, opposite to the first direction, to retract the piston rod in a direction away from the syringe receiving portion;
the apparatus being configured to:

move the anvil in the second direction, opposite the first direction, to retract a piston, by a first distance, when an orifice of a syringe connected to the apparatus is not submerged in a liquid to be dispensed; and to move the anvil in the first direction, to define a stroke distance of the striker, which is greater than the first distance, such that after accelerating the striker towards the anvil, movement of the striker is arrested by impact with the anvil to dispense a drop of liquid via the orifice.

16. A droplet dispensing apparatus for actuating a syringe to dispense droplets, comprising:
a piston rod adapted for connection with a piston, and
a driver comprising a solenoid and an output member, the output member arranged to be accelerated by the solenoid,
a striker attached to the piston rod,
an anvil arranged to arrest movement of the piston rod by impact of the striker on the anvil; and
wherein the output member is configured to be in contact with the piston rod such that the output member and piston rod simultaneously accelerate from a stationary condition.

17. The droplet dispensing apparatus according to claim 16, wherein the piston rod is adapted for interference fit with the piston.

\* \* \* \* \*